US010725004B2

(12) United States Patent
Maddila et al.

(10) Patent No.: US 10,725,004 B2
(45) Date of Patent: Jul. 28, 2020

(54) METHOD TO AUTO-CONFIGURE GAS DETECTORS BASED ON REAL-TIME LOCATION

(71) Applicant: Honeywell International Inc., Morris Plains, NJ (US)

(72) Inventors: Vidyasagar Baba Maddila, Bangalore (IN); Tijo Thomas, Bangalore (IN); Kurian George, Bangalore (IN); Arunkumar Kamalakannan, Chennai (IN); Suryaramya Talluri, Bangalore (IN); Swapna Illuru, Bangalore (IN)

(73) Assignee: Honeywell International Inc., Morris Plains, NJ (US)

( * ) Notice: Subject to any disclaimer, the term of this patent is extended or adjusted under 35 U.S.C. 154(b) by 25 days.

(21) Appl. No.: 16/146,655

(22) Filed: Sep. 28, 2018

(65) Prior Publication Data

US 2019/0094193 A1 Mar. 28, 2019

Related U.S. Application Data

(63) Continuation of application No. 14/730,794, filed on Jun. 4, 2015, now Pat. No. 10,156,552.

(30) Foreign Application Priority Data

May 13, 2015 (IN) ............................ 1340/DEL/2015

(51) Int. Cl.
G01N 33/00 (2006.01)
G08B 21/14 (2006.01)
(52) U.S. Cl.
CPC ..... G01N 33/0006 (2013.01); G01N 33/0063 (2013.01); G08B 21/14 (2013.01)

(58) Field of Classification Search
CPC .......... G01N 33/0006; G01N 33/0063; G01N 33/0009; G01N 2201/0221
See application file for complete search history.

(56) References Cited

U.S. PATENT DOCUMENTS 5,060,308 A 10/1991 Bieback
5,568,121 A 10/1996 Lamensdorf
(Continued)

FOREIGN PATENT DOCUMENTS

AU 2015385701 A1 10/2017
BR PI1105634 7/2015
(Continued)

OTHER PUBLICATIONS

U.S. Appl. No. 14/730,794, Office Action, dated Jan. 16, 2018, 12 pages.

(Continued)

Primary Examiner — Natalie Huls
(74) Attorney, Agent, or Firm — Alston & Bird LLP

(57) ABSTRACT

Embodiments relate generally to systems and methods for determining the location of a gas detector device, wherein the location may be within a predefined location zone, and automatically configuring the gas detector device based on the location zone. Each location zone in a facility may be associated with a configuration for the gas detector device. The location of the gas detector device may be monitored by a central station, and when it is determined that a gas detector device has moved from one location zone to another, the configuration of the gas detector device may be updated accordingly. Additionally, other parameters may be monitored by the central station and/or the gas detector device to determine the appropriate configuration of the gas detector device.

7 Claims, 2 Drawing Sheets

(56) References Cited

U.S. PATENT DOCUMENTS

| | | | |
|---|---|---|---|
| 5,767,390 A | 6/1998 | Chapman, IV | |
| 5,771,004 A | 6/1998 | Suppelsa et al. | |
| 5,922,943 A | 7/1999 | Chapman, IV | |
| 6,053,030 A | 4/2000 | Whynall et al. | |
| 6,114,964 A | 9/2000 | Fasano | |
| 6,138,512 A | 10/2000 | Roberts et al. | |
| 6,182,497 B1 | 2/2001 | Krajci | |
| 6,198,390 B1 | 3/2001 | Schlager et al. | |
| 6,252,510 B1 | 6/2001 | Dungan | |
| 6,415,646 B1 | 7/2002 | Kessel et al. | |
| 6,670,887 B2 | 12/2003 | Dungan | |
| 6,772,071 B2 | 8/2004 | Gilbert et al. | |
| 6,885,299 B2 | 4/2005 | Cooper et al. | |
| 7,019,637 B1 | 3/2006 | Johnson et al. | |
| 7,080,544 B2 | 7/2006 | Stepanik et al. | |
| 7,091,852 B2 | 8/2006 | Mason et al. | |
| 7,191,097 B1 | 3/2007 | Lee et al. | |
| 7,221,928 B2 | 5/2007 | Laird et al. | |
| 7,292,189 B2 | 11/2007 | Orr et al. | |
| 7,345,582 B2 | 3/2008 | Gould | |
| 7,483,917 B2 | 1/2009 | Sullivan et al. | |
| 7,522,043 B2 | 4/2009 | English et al. | |
| 7,528,711 B2 | 5/2009 | Kates | |
| 7,605,696 B2 | 10/2009 | Quatro | |
| 7,609,159 B2 | 10/2009 | Benson et al. | |
| 7,688,198 B2 | 3/2010 | Amidi | |
| 7,848,732 B2 | 12/2010 | Thomas | |
| 7,874,198 B2 | 1/2011 | Groves | |
| 7,904,244 B2 | 3/2011 | Sugla | |
| 7,934,412 B2 | 5/2011 | Prince | |
| 7,994,926 B2 | 8/2011 | Longman et al. | |
| 8,099,130 B1 | 1/2012 | Halla et al. | |
| 8,350,693 B2 | 1/2013 | Mcsheffrey et al. | |
| 8,400,317 B2 | 3/2013 | Johnson et al. | |
| 8,442,801 B2 | 5/2013 | Gonia et al. | |
| 8,560,645 B2 | 10/2013 | Linden et al. | |
| 8,885,559 B2 | 11/2014 | Schmidt et al. | |
| 9,612,195 B1 | 4/2017 | Friedman | |
| 9,978,251 B2 | 5/2018 | Gonia et al. | |
| 2002/0008625 A1 | 1/2002 | Adams et al. | |
| 2003/0214410 A1 | 11/2003 | Johnson et al. | |
| 2004/0056771 A1 | 3/2004 | Dungan | |
| 2004/0149918 A1 | 8/2004 | Craig et al. | |
| 2004/0203904 A1 | 10/2004 | Gwon et al. | |
| 2004/0204915 A1 | 10/2004 | Steinthal et al. | |
| 2004/0215532 A1 | 10/2004 | Boman et al. | |
| 2005/0057370 A1 | 3/2005 | Warrior et al. | |
| 2006/0082462 A1 | 4/2006 | Crook | |
| 2007/0008099 A1 | 1/2007 | Kimmel et al. | |
| 2007/0050157 A1 | 3/2007 | Kahn et al. | |
| 2007/0168127 A1 | 7/2007 | Zaruba et al. | |
| 2008/0122641 A1 | 5/2008 | Amidi | |
| 2008/0130604 A1 | 6/2008 | Boyd | |
| 2008/0168826 A1 | 7/2008 | Saidi et al. | |
| 2009/0139299 A1 | 6/2009 | Prince | |
| 2009/0188302 A1 | 7/2009 | Rolff et al. | |
| 2009/0212995 A1 | 8/2009 | Wu et al. | |
| 2010/0081411 A1 | 4/2010 | Montenero | |
| 2011/0037599 A1 | 2/2011 | Johnson et al. | |
| 2011/0161044 A1 | 6/2011 | Gonia et al. | |
| 2011/0251800 A1 | 10/2011 | Wilkins | |
| 2012/0191349 A1 | 7/2012 | Lenz et al. | |
| 2012/0280818 A1 | 11/2012 | Johnson et al. | |
| 2012/0310547 A1 | 12/2012 | Cristoforo | |
| 2013/0260792 A1 | 10/2013 | Johnson et al. | |
| 2013/0328697 A1 | 12/2013 | Lundy | |
| 2013/0331028 A1 | 12/2013 | Kuehnel et al. | |
| 2014/0031802 A1 | 1/2014 | Melsky et al. | |
| 2014/0162692 A1 | 6/2014 | Li et al. | |
| 2014/0253326 A1 | 9/2014 | Cho et al. | |
| 2014/0254549 A1 | 9/2014 | Lee et al. | |
| 2014/0349707 A1 | 11/2014 | Bang | |
| 2015/0075256 A1 | 3/2015 | Basham et al. | |
| 2015/0177208 A1 | 6/2015 | Murphy | |
| 2016/0381440 A1 | 12/2016 | Davis | |
| 2017/0339741 A1 | 11/2017 | K et al. | |
| 2018/0075728 A1 | 3/2018 | Liu et al. | |

FOREIGN PATENT DOCUMENTS

| | | |
|---|---|---|
| CA | 2760872 A1 | 6/2012 |
| CN | 101361321 A | 2/2009 |
| CN | 101983515 A | 3/2011 |
| CN | 202082628 U | 12/2011 |
| CN | 102937610 A | 2/2013 |
| CN | 102608564 B | 4/2016 |
| CN | 107005806 A | 8/2017 |
| CN | 107534926 A | 1/2018 |
| CN | 107851360 A | 3/2018 |
| EP | 2339556 A1 | 6/2011 |
| EP | 1929455 B1 | 12/2011 |
| EP | 2461176 B1 | 10/2016 |
| EP | 3228068 | 10/2017 |
| EP | 3269180 A1 | 1/2018 |
| EP | 3295442 A1 | 3/2018 |
| IN | 032013 | 1/2013 |
| JP | 09-009339 A | 1/1997 |
| JP | 2004-242129 A | 8/2004 |
| JP | 2009-092594 A | 4/2009 |
| JP | 2010-236866 A | 10/2010 |
| JP | 6058885 B2 | 1/2017 |
| RU | 46597 U1 | 7/2005 |
| RU | 2602700 C2 | 11/2016 |
| SU | 1621067 A1 | 1/1991 |
| WO | 2005/001788 A1 | 1/2005 |
| WO | 2011/019525 A2 | 2/2011 |
| WO | 2016/089734 A1 | 6/2016 |
| WO | 2016/141582 A1 | 9/2016 |
| WO | 2016/182878 A1 | 11/2016 |

OTHER PUBLICATIONS

U.S. Appl. No. 14/730,794, Notice of Allowance, dated Jun. 27, 2018, 10 pages.
U.S. Appl. No. 15/557,766, Notice of Allowance, dated May 25, 2018, 13 pages.
U.S. Appl. No. 14/730,794, Restriction Requirement, dated Jan. 23, 2017, 9 pages.
U.S. Appl. No. 14/730,794, Office Action, dated Apr. 18, 2017, 18 pages.
U.S. Appl. No. 14/730,794, Final Office Action, dated Aug. 30, 2017, 12 pages.
U.S. Appl. No. 12/959,250, Office Action, dated Oct. 4, 2012, 40 pages.
U.S. Appl. No. 12/959,250, Notice of Allowance, dated Jan. 18, 2013, 12 pages.
U.S. Appl. No. 12/695,736, Notice of Allowance, dated Oct. 18, 2017, 5 pages.
U.S. Appl. No. 12/695,736, Advisory Action, dated Dec. 18, 2013, 3 pages.
United States Patent Application Serial filed Sep. 12, 2017, 19 pages, U.S. Appl. No. 15/557,766.
United States Patent Application Serial filed Jun. 2, 2017, 19 pages, U.S. Appl. No. 15/532,620.
United States Patent Application Serial Decision on Appeal, dated Aug. 1, 2017, 8 pages, U.S. Appl. No. 12/695,736.
United Arab Emirates Patent Application No. 1221/2011, Notice of Acceptance, dated May 4, 2017, 2 pages.
U.S. Appl. No. 12/695,736, Office Action, dated Oct. 11, 2013, 16 pages.
U.S. Appl. No. 12/695,736, Office Action, dated Mar. 2, 2015, 27 pages.
U.S. Appl. No. 12/695,736, Office Action, dated Jun. 7, 2013, 16 pages.
U.S. Appl. No. 12/695,736, Office Action, dated Jun. 10, 2015, 36 pages.
U.S. Appl. No. 12/695,736, Office Action, dated Jan. 30, 2014, 19 pages.

(56) References Cited

OTHER PUBLICATIONS

U.S. Appl. No. 12/695,736, Office Action, dated Aug. 19, 2014, 21 pages.
U.S. Appl. No. 12/695,736, Examiner's Answer to Appeal Brief, dated Mar. 22, 2016, 34 pages.
U.S. Appl. No. 12/695,736, Examiner's 2nd or Subsequent Answer to Appeal Brief, dated Apr. 8, 2016, 34 pages.
U.S. Appl. No. 12/695,736, Advisory Action, dated Nov. 7, 2014, 7 pages.
U.S. Appl. No. 12/695,736, Advisory Action, dated Aug. 11, 2015, 7 pages.
True Wireless TM Gas Transmitters, 2008, Retrieved from the Internet:<www.gastronics.com>, 2 pages.
Sierra Monitor Corporation, Sentry 8 Channel Gas Detection Controller Data Sheet, http://www.sierramonitor.com/assets/blt76714116742534fe/SMC%20Data%20Sheet%20-%20Sentry%20Controller.pdf, 2009, 4 pages.
Safe-T-Cube, Retrieved from the Internet on: Sep. 19, 2009; Retrieved from the Internet: <http://nutech-australia.com.au/nutech-australia.com.au/Neotronics>, 1 page.
Russia Patent Application No. 2011149131, Office Action, dated Sep. 23, 2015, 12 pages.
Russia Patent Application No. 2011149131, Office Action, dated Feb. 19, 2016, 14 pages.
Russia Patent Application No. 2011149131, Notice of Allowance, dated Jun. 14, 2016, 23 pages.
Neotronics Safe-T-Cube, 2005, Retrieved from the Internet on Apr. 5, 2017; Retrieved from the Internet: <http://www.abstrumenti.com/datasheet/safe-t-cube.pdf>., 4 pages.
Junjie Chen et al., "A Weighted Compensated Localization Algorithm of Nodes in Wireless Sensor Networks", Advanced Computational Intelligence, Aug. 25-28, 2010, Zushou, Juiangsu, China, pp. 379-384.
Japan Patent Application No. 2011-263814, Office Action, dated Aug. 4, 2015, 10 pages.
Japan Patent Application No. 2011-263814, Office Action, dated Apr. 12, 2016, 7 pages.
Japan Patent Application No. 2011-263814, Notice of Allowance, dated Nov. 9, 2016, 3 pages.
International Application No. PCT/US2016/031113, Written Opinion of the International Searching Authority, dated Nov. 7, 2016, 8 pages.
International Application No. PCT/US2016/031113, International Search Report, dated Nov. 7, 2016, 5 pages.
International Application No. PCT/US2016/031113, International Preliminary Report on Patentability, dated Nov. 14, 2017, 9 pages.
International Application No. PCT/US2015/062916, Written Opinion of the International Searching Authority, dated Feb. 29, 2016, 7 pages.
International Application No. PCT/US2015/062916, International Search Report, dated Feb. 29, 2016, 3 pages.
International Application No. PCT/US2015/062916, International Preliminary Report on Patentability, dated Jun. 6, 2017, 8 pages.
International Application No. PCT/US2015/031113, Written Opinion of the International Searching Authority, dated Jul. 11, 2016, 8 pages.
International Application No. PCT/US2015/031113, International Search Report, dated Jul. 11, 2016, 5 pages.
International Application No. PCT/CN2015/074089, Written Opinion of the International Searching Authority, dated Oct. 28, 2015, 4 pages.
International Application No. PCT/CN2015/074089, International Search Report, dated Oct. 28, 2015, 3 pages.
International Application No. PCT/CN2015/074089, International Preliminary Report on Patentabilily, dated Sep. 12, 2017, 5 pages.
Europe Patent Application No. 16723898.9, Communication pursuant to Rule 161(1) and 162 EPC, dated Jan. 1, 2018, 3 pages.
Europe Patent Application No. 15884265.8, Communication pursuant to Rule 161(1) and 162 EPC, dated Dec. 15, 2017, 3 pages.
Europe Patent Application No. 15816952.4, Invitation to file a search results or a statement of non-availablity pursuant to Rule 70b(1) EPC, dated Feb. 27, 2018, 1 page.
Europe Patent Application No. 15816952.4, Communication Pursuant to Rules 161(1) and 162 EPC, dated Jul. 11, 2017, 2 pages.
Europe Patent Application No. 11191449, Intention to Grant, dated Jun. 23, 2016, 19 pages.
Europe Patent Application No. 11191449, Examination Report, dated May 5, 2015, 4 pages.
Europe Patent Application No. 11191449, Examination Report, dated May 21, 2012, 8 pages.
Europe Patent Application No. 11191449, European Search Report, dated May 8, 2012, 4 pages.
Europe Patent Application No. 11191449, Decision to Grant, dated Sep. 29, 2016, 2 pages.
Europe Patent Application No. 10193394.3, Summons to Attend Oral Hearings, mailed Dec. 8, 2016, 8 pages.
Europe Patent Application No. 10193394.3, Search Report, dated Apr. 5, 2011, 3 pages.
Europe Patent Application No. 10193394.3, Examination Report, dated Jun. 30, 2016, 6 pages.
Europe Patent Application No. 10193394.3, Examination Report, dated Apr. 21, 2011, 3 pages.
Europe Patent Application No. 10193394.3, Examination Report, dated May 3, 2017, 7 pages.
Europe Patent Application No. 10193394.3, Decision to Refuse, dated Jul. 20, 2017, 33 pages.
Elisabetta Farella et al.,"Aware and smart environments: The Casanetta project", Microelectronics Journal 41 (2010), pp. 697-702.
China Patent Application No. 201110462147.9, Office Action, dated Oct. 30, 2014, 9 pages.
China Patent Application No. 201110462147.9, Office Action, dated Jul. 30, 2015, 4 pages.
China Patent Application No. 201110462147.9, Notification to Grant Patent Right, dated Feb. 5, 2016, 2 pages.
Canada Patent Application No. 2760872, Office Action, dated Apr. 5, 2017, 3 pages.
Canada Patent Application No. 2760872, Notice of Allowance, dated Jan. 16, 2018, 1 page.

METHOD TO AUTO-CONFIGURE GAS DETECTORS BASED ON REAL-TIME LOCATION

CROSS-REFERENCE TO RELATED APPLICATIONS

This application is a continuation of U.S. application Ser. No. 14/730,794, filed Jun. 4, 2015 and entitle "Method To Auto-Configure Gas Detectors Based On Real-Time Location", which claims priority to and the benefit of India Provisional Application Serial No. 1340/DEL/2015, filed May 13, 2015 in the India Patent Office and entitled "Method To Auto-Configure Gas Detectors Based On Real-Time Location", the entire contents of which are hereby incorporated by reference in their entirety.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Gas detector devices are typically used in environments containing, of having the potential to contain, harmful gases. In a safety related wireless gas detection environment, tracking a worker in a facility is important. Some facilities using wireless gas detection may comprise multiple different areas where different gasses, or different levels of gasses, may be present, wherein workers may be required to move between the different areas during their daily activities.

SUMMARY

Aspects of the disclosure may include a method for configuring a gas detector device, the method comprising: detecting gas, by the gas detector device, in a first location zone, wherein the gas detector device is configured for the first location zone; determining that the gas detector device has entered a second location zone; configuring the gas detector device for the second location zone; detecting gas in the second location zone; and alerting a user when the detected gas is over a threshold, wherein the threshold is defined by the configuration of the gas detector device.

In some embodiments, the gas detector device comprises a plurality of gas sensors, and configuring the gas detector device comprises deactivating one or more of the gas sensors and activating one or more of the gas sensors. In some embodiments, configuring the gas detector device comprises changing the threshold for alert. In some embodiments, the method further comprises determining the identity of the user of the gas detector device; and configuring the gas detector device based on the identity of the user, wherein the user's identity is associated with thresholds for alert. In some embodiments, the method further comprises determining the time of day when the gas detector device is in use; and configuring the gas detector device based on the time of day, wherein the time of day is associated with thresholds for alert and associated with types of gas that should be detected. In some embodiments, the method further comprises determining the type of the gas detector device. In some embodiments, the method further comprises defining a plurality of location zones within a facility, wherein each location zone is associated with a configuration for the gas detector device. In some embodiments, determining the location of the gas detector device is accomplished using global positioning systems. In some embodiments, determining the location of the gas detector device is accomplished using wireless triangulation systems.

Additional aspects of the disclosure may include embodiments of a method for configuring a gas detector device, the method comprising powering on the gas detector device; configuring the gas detector device in a default configuration; determining that the gas detector device has entered a first location zone; configuring the gas detector device for the first location zone; determining that the gas detector device has entered a second location zone; and configuring the gas detector device for the second location zone, wherein each location zone is associated with a configuration for the gas detector device, and wherein configuring comprises defining threshold limits, and indicating gas sensor activation.

In some embodiments, determining the location of the gas detector device is accomplished using global positioning systems. In some embodiments, determining the location of the gas detector device is accomplished using wireless triangulation systems. In some embodiments, the method further comprises defining a plurality of location zones within a facility, wherein each location zone is associated with a configuration for the gas detector device. In some embodiments, the gas detector device comprises a plurality of gas sensors, and wherein configuring the gas detector device comprises deactivating one or more of the gas sensors and activating one or more of the gas sensors.

Other aspects of the disclosure may include embodiments of a method for configuring a gas detector device, the method comprising receiving, by a central station, detected gas data from the gas detector device; receiving, by the central station, location data from the gas detector device; determining that the gas detector device has moved from a first location zone to a second location zone based on the received location data; accessing, by the central station, configuration instructions associated with the second location zone; and sending, by the central station, the configuration instructions associated with the second location zone to the gas detector device, wherein the gas detector device uses the configuration instructions to update the configuration of the gas detector device.

In some embodiments, receiving location data from the gas detector device occurs approximately every two minutes. In some embodiments, the configuration instructions comprise defining threshold limits, and indicating gas sensor activation. In some embodiments, the method further comprises storing, by the central station, the received location data for future reference, wherein determining that the gas detector device has moved from a first location zone to a second location zone based on the received location data comprises comparing the currently received location data to previously sorted location data. In some embodiments, the method further comprises sending a confirmation message to the gas detector device before sending the configuration instructions; and receiving a response from the gas detector device. In some embodiments, the method further comprises defining a plurality of location zones within a facility, wherein each location zone is associated with a configuration for the gas detector device; and storing, by the central station, the location zone information and associations.

These and other features will be more clearly understood from the following detailed description taken in conjunction with the accompanying drawings and claims.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

Figure 1:
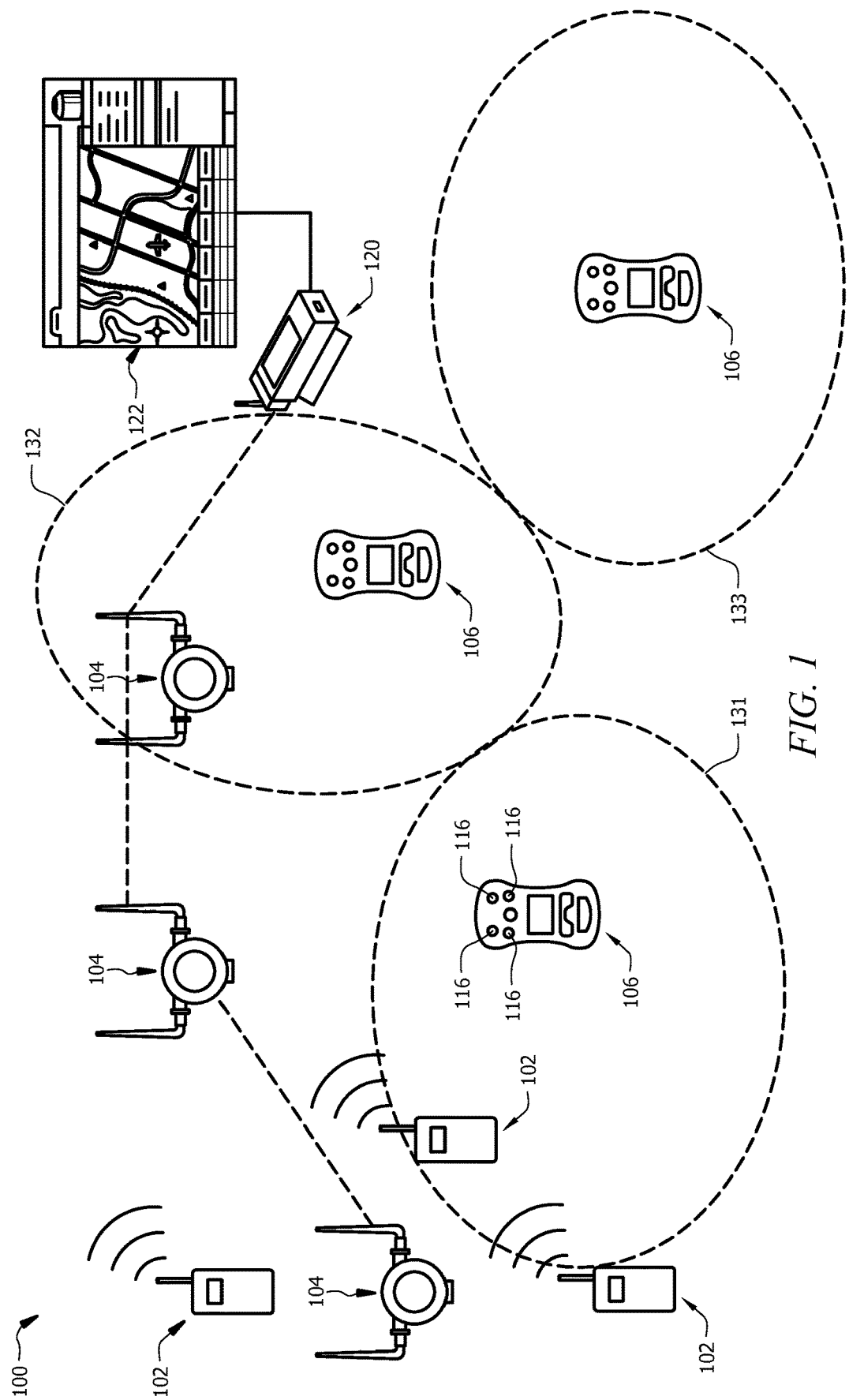
FIG. 1 illustrates a facility comprising a plurality of location zones according to an embodiment of the disclosure.

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

The following brief definition of terms shall apply throughout the application:

The term "comprising" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a non-exclusive example;

The terms "about" or "approximately" or the like, when used with a number, may mean that specific number, or alternatively, a range in proximity to the specific number, as understood by persons of skill in the art field; and If the specification states a component or feature "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

Embodiments of the disclosure relate to systems and methods for configuring gas detector devices based on location. Typically, if a worker moves from one area or zone of a facility to another, the gas detector device carried by the user may be required to come out of service for the configuration to be changed. Alternatively, a user may be required to switch to a new gas detector device that is configured for the new area or zone. These steps may take time out of the workers day to ensure that the device he is carrying is configured correctly. Also, it may be possible for a worker to carry a device with inappropriate configuration into an area, which may lead to safety issues if a gas alarm is not raised at the intended levels for that area. Device availability may be reduced if workers have to switch devices at each area or zone.

Embodiments of the disclosure may comprise systems and methods for determining the location of a gas detector device, wherein the location may be within a predefined location zone, and automatically configuring the gas detector device based on the location zone. Each location zone in a facility may be associated with a configuration for the gas detector device. The location of the gas detector device may be monitored by a central station, and when it is determined that a gas detector device has moved from one location zone to another, the configuration of the gas detector device may be updated accordingly. Additionally, other parameters may be monitored by the central station and/or the gas detector device to determine the appropriate configuration of the gas detector device.

Additionally, similar methods and systems may be applied to any personal protective equipment (PPE) device, where the location of the PPE device may be determined using similar methods. One or more PPE device may be used or required in a specific zone, and may be monitored within that zone. Additionally, some PPE device may require alteration when moving from zone to zone.

Referring now to FIG. 1, a facility 100 is shown, wherein within the facility 100, a plurality of location zones 131, 132, 133 have been defined. The location zones 131, 132, 133 may he defined based on the type(s) of gas to be detected in that area, levels of gas anticipated in that area, types of equipment in that number of workers in that area, personal protection equipment required for that area, among other similar distinctions. For example, the criticality of the zone, as well as the historical incident information for the zone, may be taken into consideration when defining the zone boundaries and requirements. The location zones 131, 132, 133 may be predefined, and the zone definitions may be stored at the central station 120. In some embodiments, the location zones 131, 132, 133 may be dynamically changed based on changes that occur within the facility.

In some embodiments, the facility 100 may comprise a communication network, which may comprise one or more access points 104, one or more location beacons 102, and a central station 120, wherein the central station 120 may receive data and information from devices within the facility 100 and monitor that information. Additionally, the central station 120 may comprise a user interface 122, wherein the received data and information may be displayed by the user interface 122.

In some embodiments, one of more gas detector device 106 may be carried by a user within the facility 100. The gas detector device 106 may detect the concentration of harmful gases in the area a user is working in. The gas detector device 106 may be operable to alert the user when the detected gas exceeds a threshold for a particular gas. In some embodiments, the gas detector device 106 may wirelessly communicate with the one or more access point 104, wherein the gas detector device 106 may communicate data to the central station 120 via the one or more access point 104. The gas detector device 106 may communicate gas concentration data, alert status, and other information to the central station 120. In some embodiments, the gas detector device 106 may communication location information to the central station 120.

In some embodiments, the gas detector device 106 may communicate with the location beacons 102 to determine the location of the gas detector device 106 within the facility 100. The location of the gas detector device 106 may be determined by a triangulation algorithm using information from the beacons 102. In some embodiments, the beacons 102 may communicate directly with the central station 120, while in other embodiments, the beacons 102 may communicate information to the gas detector device 106, wherein the gas detector device 106 may then communicate the information to the central station 120. In an alternative embodiment, the location of the gas detector device 106 may be determined using a wireless fidelity (Wi-Fi) connection between the gas detector device 106 and the one or more access points 104. In some embodiments, the location of the gas detector device 106 may be determined using a global positioning system (GPS).

In some alternative embodiments, the location of the gas detector device 106 may be estimated based on the access point 104 that the device is communicating with. For example, the access point 104 may be located within a location zone 131, 132, 133, and any gas detector devices 106 that are communicating with that access point 104 may be estimated to be in the same location zone as the access point 104. This may be a simpler, but less exact, method for determining the location of the gas detector device 106. In some other embodiments, the gas detector device 106 may communicate with neighboring gas detectors 106, as the gas detector device 106 may not have connectivity to an access point 104 directly. In this case, the neighboring detectors 106 can help in identifying the location of the gas detector device 106 by routing to its parent node in the network 100, i.e. an access point 104.

In a facility 100 where one or more location zones 131, 132, 133 have been defined, the location of the gas detector device 106 may be determined to be within one of the location zones 131, 132, 133 of the facility 100. In some embodiments, the location zones 131, 132, 133 may be based on the definition of the location zone, including type of gas to be detected in that area, levels of gas anticipated in that area, types of equipment in that area, personal protection equipment required for that area, among other similar distinctions. In some embodiments, the configuration may be based on the type of gas detector device 106, wherein each gas detector device 106 may comprise different gas sensors 116 and capabilities. In some embodiments, the configuration may be based on the date and/or time of day, wherein the processes taking place within each location zone of the facility, and therefore the potential for harmful gases and the identity of those gases in each zone, may vary based on the day and/or time of day. In some embodiments, the configuration may be based on the identification of the user, wherein a user may or may have health issues that affect the threshold of exposure to one or more harmful gases before an alert is triggered. In some embodiments, the identification of the user may be input by the user to the gas detector device 106.

In some embodiments, configuring the gas detector device 106 may comprise updating the threshold limits for alert for the gas sensor(s) 116 in the gas detector device 106. In some embodiments, configuration may comprise activating or deactivating gas sensors 116 in the gas detector 106. For example, a first location zone may require a first gas to be sensed, and therefore a first gas sensor 116 to be activated, while a second location zone may require a second gas to be sensed, and therefore a second gas sensor 116 to be activated (and the first gas sensor 116 to be deactivated). In some embodiments, a combination of gas sensors 116 may be activated at a time, allow the gas detector device 116 to sense a plurality of gases.

Each possible configuration for the gas detector device(s) 106 may be stored at the central station 120, wherein the central station 120 may receive and/or determine the necessary information to provide a configuration for the gas detector device 106. The central station 120 may receive location information for the gas detector device 106 and then determine in which location zone 131, 132, 133 the gas detector is located. The central station 120 may periodically receive location information from each gas detector device 106 in the facility 100 and determine when a gas detector device 106 moves from on location zone to another.

In some embodiments, the location zones 131, 132, 133 may be associated with different configurations for the gas detector device(s) 106, while in other embodiments, some of the location zones 131, 132, 133 may be associated with similar configurations.

In some embodiments, updating the configuration of one or more gas detector devices 106 may be initiated by a facility-wide roll out of new configuration requirements. This may occur when safety guidelines are updates, new processes occur in the facility 100, or when any other change occurs that would require the gas detector device(s) 106 to operate differently. For example, the threshold limits may be changed or updated, and/or different gasses may be present in the facility. If a facility-wide change is made, the central station 120 may communicate the new configuration information to the gas detector devices 106 throughout the facility 100, and the updates may happen automatically, without requiring the devices 106 to come out of service.

Figure 2:
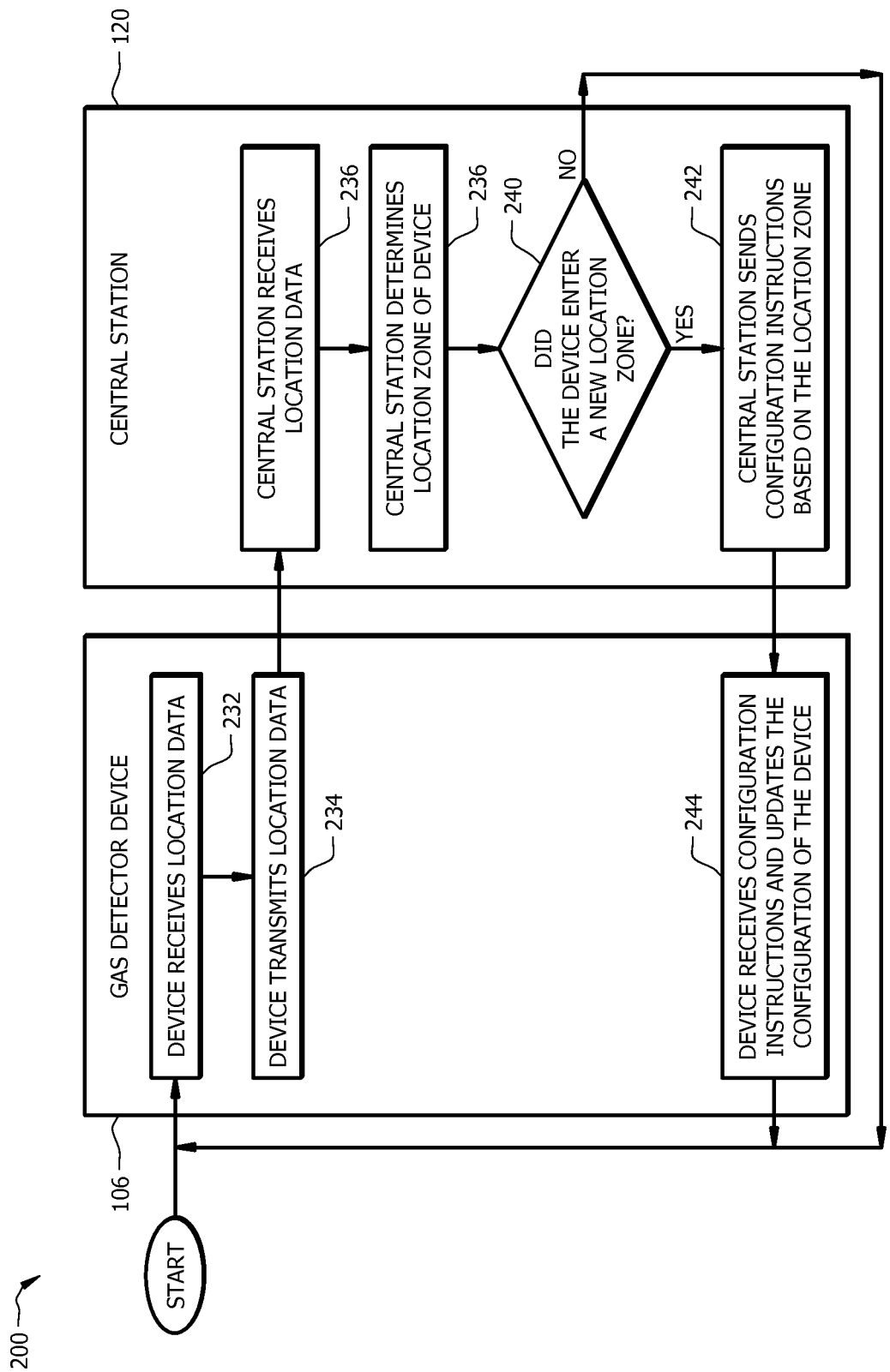
FIG. 2 illustrates a method for configuring a gas detector device according to an embodiment of the disclosure.

Referring now to FIG. 2, a method 200 for configuring a gas detector device 106 is described. At step 232, the gas detector device 106 may receive location data from one or more location beacons and/or one or more access points (as described in FIG. 1). At step 234, the gas detector device 106 may then transmit the location data to the central station 120. In some embodiments, the gas detector device 106 may communicate with the central station 120 via a wireless connection, such as via one or more access points (as described in FIG. 1). At step 236, the central station 120 may receive the location data, and at step 238, the central station may determine the location zone of the gas detector device 106 based on the location data. In some embodiments, the plurality location zones may be predefined and stored at the central station 120. At step 240, the central station 120 may determine if the gas detector device has entered a new location zone, wherein the previously determine location zone of the device may be stored by the central station 120. If the central station 120 determines that the gas detector device 106 has not entered a new location zone (NO), the method 200 may be repeated from the beginning, wherein the central station 120 may periodically monitor the location of the gas detector device 106.

If the central station 120 determines that the gas detector device 106 has entered a new location zone (YES), at step 242, the central station 120 may send configuration instructions to the gas detector device 106 based on the new location zone. In some embodiments, the central station 120 may access a database wherein the location zones are associated with a configuration and stored in the database. At step 244, the gas detector device 106 may receive the configuration instructions from the central station 120, and the gas detector device 106 may automatically update the configuration of the device 106 accordingly. After the gas detector device 106 has updated, the method may be repeated from the beginning, wherein the central station 120 may periodically monitor the location of the gas detector device 106. In some embodiments, the method may be repeated approximately every two minutes. In some embodiments, the method may be repeated approximately every one minute. In some embodiments, when the gas detector device 106 is in an alarm mode, the method 200 may be repeated more frequently, such as every 10 seconds.

In some embodiments, a user may be able to indicate that the user, and therefore the gas detector device 106, is entering a new location zone. This may initiate the method 200 manually, wherein the device 106 may then be automatically updated to the configuration for the new location zone. In some embodiments, after step 242 and before step 244, the gas detector device 106 may display a confirmation message to the user and alert the user that the configuration of the device 106 should be updated. In some embodiments, this message/alert may notify a user that updates have been made to the configuration of the gas detector device 106. In some embodiments, the user may be required to positively respond to the confirmation message before the gas detector device 106 will complete the configuration updates. If a user responds negatively (or does not respond) to the confirmation message, and does not allow the updates, the gas detector device 106 may send a notification to the central monitoring station 120 that the updates have not been implemented. A safety manager may then be able to take appropriate action to avoid any incidents. In some embodiments, the user's response to the confirmation message may be recorded by the central station 120 for future reference. Additionally, all updates made to the gas detector device 106 may be recorded and stored by the central station 120.

In some embodiments, when the gas detector device 106 is first powered on, the device 106 may comprise a default configuration. Then, when it is determined that the gas detector device 106 has entered a first location zone, the configuration of the device 106 may be updated for the first location zone. In some embodiments, the default configuration may comprise a "conservative" configuration, which may include standard threshold limits that are not customized for a specific location. Additionally, in gas detector devices 106 with multiple gas sensors, the default configuration may have all gas sensors activated.

Referring back to FIG. 1, embodiments of the disclosure may comprise methods for configuring a gas detector device 106. The method may comprise detecting gas, by the gas detector device 106, in a first location zone 131, wherein the gas detector device 106 is configured for the first location zone 131. The method may comprise determining that the gas detector device 106 has entered a second location zone 132 and configuring the gas detector device 106 for the second location zone 132. The method may then comprise detecting gas, by the gas detector device 106, in the second location zone 132, and alerting a user when the detected gas is over a threshold, wherein the threshold is defined by the configuration of the gas detector device 106.

In some embodiments, the gas detector device 106 may comprise a plurality of gas sensors 116, wherein configuring the gas detector device 106 comprises deactivating one or more of the gas sensors 116 and activating one or more of the gas sensors 116. In some embodiments, configuring the gas detector device 106 may comprise changing the threshold for alert. In some embodiments, the method may further comprise determining the identity of the user of the gas detector device 106, and configuring the gas detector device 106 based on the identity of the user, wherein the user's identity is associated with thresholds for alert. In some embodiments, the method may further comprise determining the time of day when the gas detector device 106 is in use, and configuring the gas detector device 106 based on the time of day, wherein the time of day is associated with thresholds for alert and associated with types of gas that should be detected. In some embodiments, the method may further comprise determining the type of the gas detector device 106. In some embodiments, the method may further comprise defining a plurality of location zones 131, 132, 133 within a facility 100, wherein each location zone is associated with a configuration for the gas detector device 106. In some embodiments, determining the location of the gas detector device 106 is accomplished using global positioning systems. In some embodiments, determining the location of the gas detector device 106 is accomplished using wireless triangulation systems.

Embodiments of the disclosure may comprise additional methods for configuring a gas detector device 106. The method may comprise powering on the gas detector device 106 and configuring the gas detector device 106 in a default configuration. The method may then comprise determining that the gas detector device 106 has entered a first location zone 131, and configuring the gas detector device 106 for the first location zone 131. The method may then comprise determining that the gas detector device 106 has entered a second location zone 132, and configuring the gas detector device 106 for the second location zone 132, wherein each location zone 131 and 132 is associated with a configuration for the gas detector device 106, and wherein configuring comprises defining threshold limits, and indicating gas sensor activation.

In some embodiments, determining the location of the gas detector device 106 is accomplished using global positioning systems. In some embodiments, determining the location of the gas detector device 106 is accomplished using wireless triangulation systems. In some embodiments, the method may further comprise defining a plurality of location zones 131, 132, 133 within a facility 100, wherein each location zone is associated with a configuration for the gas detector device 106. In some embodiments, the gas detector device 106 comprises a plurality of gas sensors 116, wherein configuring the gas detector device 106 comprises deactivating one or more of the gas sensors 116 and activating one or more of the gas sensors 116.

Embodiments of the disclosure may comprise additional methods for configuring a gas detector device 106. The method may comprise receiving, by a central station 120, detected gas data from the gas detector device 106 and receiving, by the central station 120, location data from the gas detector device 106. The method may comprise determining that the gas detector device 106 has moved from a first location zone 131 to a second location zone 132 based on the received location data The method may comprise accessing, by the central station 120, configuration instructions associated with the second location zone 132, and sending, by the central station 120, the configuration instructions associated with the second location zone 132 to the gas detector device 106, wherein the gas detector device 106 uses the configuration instructions to update the configuration of the gas detector device 106.

In some embodiments, receiving location data from the gas detector device 106 occurs approximately every two minutes. In some embodiments, the configuration instructions comprise defining threshold limits, and indicating gas sensor activation. In some embodiments, the method further comprises storing, by the central station 120, the received location data for future reference, and the step of determining that the gas detector device 106 has moved from a first location zone 131 to a second location zone 132 based on the received location data comprises comparing the currently received location data to previously sorted location data. In some embodiments, the method further comprises sending a confirmation message to the gas detector device 106 before sending the configuration instructions, and receiving a response from the gas detector device 106. In some embodiments, the method further comprises defining a plurality of location zones 131, 132, 133 within a facility 100, wherein each location zone is associated with a configuration for the gas detector device 106, and storing, by the central station 120, the location zone information and associations.

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow, that scope including all equivalents of the subject matter of the claims. Each and every claim is incorporated as further disclosure into the specification and the claims are embodiment(s) of the present invention(s). Furthermore, any advantages and features described above may relate to specific embodiments, but shall not limit the application of such issued claims to processes and structures accomplishing any or all of the above advantages or having any or all of the above features.

Additionally, the section headings used herein are provided for consistency with the suggestions under 37 C.F.R. 1.77 or to otherwise provide organizational cues. These headings shall not limit or characterize the invention(s) set out in any claims that may issue from this disclosure. Specifically and by way of example, although the headings might refer to a "Field," the claims should not be limited by the language chosen under this heading to describe the so-called field. Further, a description of a technology in the "Background" is not to be construed as an admission that certain technology is prior art to any invention(s) in this disclosure. Neither is the "Summary" to be considered as a limiting characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of the claims shall be considered on their own merits in light of this disclosure, but should not be constrained by the headings set forth herein.

Use of broader terms such as comprises, includes, and having should be understood to provide support for narrower terms such as consisting of, consisting essentially of, and comprised substantially of. Use of the term "optionally," "may," "might," "possibly," and the like with respect to any element of an embodiment means that the element is not required, or alternatively, the element is required, both alternatives being within the scope of the embodiment(s). Also, references to examples are merely provided for illustrative purposes, and are not intended to be exclusive.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A method for configuring a gas detector device, the method comprising:
   receiving, by a central station, detected gas data from the gas detector device;
   receiving, by the central station, location data from the gas detector device; determining whether the gas detector device has moved from a first location zone to a second location zone based on the received location data;
   accessing, by the central station, configuration instructions associated with the second location zone when the gas detector device has moved to the second location zone;
   defining a plurality of location zones within a facility, wherein
      each location zone is associated with a particular configuration for the gas detector device, and
      a boundary for each location zone of the plurality of location zones is defined based on at least one or more of a criticality of an area or historical incident information of the area, a type of gas to be detected in the area, concentration levels of a gas anticipated in the area, types of equipment available in the area, a number of workers in the area, or a personal protection equipment required for the area;
   storing, by the central station, the location zone and corresponding configurations;
   and
   sending, by the central station, the configuration instructions associated with the second location zone to the gas detector device, wherein the gas detector device uses the configuration instructions to update a current configuration of the gas detector device.

2. The method of claim 1, wherein receiving the location data from the gas detector device occurs at periodic intervals of time.

3. The method of claim 1, wherein the configuration instructions comprise defining threshold limits of gas concentration and causing a plurality of gas sensors, located within the gas detector device, to activate or deactivate.

4. The method of claim 1 further comprising storing, by the central station, the received location data, wherein determining whether the gas detector device has moved from the first location zone to the second location zone based on the received location data comprises comparing currently received location data to previously stored location data.

5. The method of claim 1 further comprising:
sending a confirmation message to the gas detector device before sending the configuration instructions; and
receiving a response from the gas detector device.

6. The method of claim 1 further comprising storing, by the central station, the configuration instructions received by the gas detector device.

7. The method of claim 1, wherein the boundary for each location zone of the plurality of location zones is defined dynamically.

* * * * *